United States Patent [19]
Carr et al.

[11] Patent Number: 5,478,846
[45] Date of Patent: Dec. 26, 1995

[54] 1-PIPERIDINYL ALKANOYLANYL SULFONAMIDES FOR TREATMENT OF CARDIAC ARRHYTHMIA

[75] Inventors: Albert A. Carr; Richard C. Dage, both of Cincinnati; Thaddeus R. Nieduzak, Golf Manor; John E. Koerner; Tung Li, both of Cincinnati, all of Ohio

[73] Assignee: Merrell Dow Pharmaceuticals Inc., Cincinnati, Ohio

[21] Appl. No.: 279,623

[22] Filed: Jul. 22, 1994

Related U.S. Application Data

[63] Continuation of Ser. No. 956,752, filed as PCT/US91/03323, May 15, 1991, abandoned.

[51] Int. Cl.$^6$ .................... A61K 21/445; C07D 211/28; C07D 211/32
[52] U.S. Cl. .................. 514/330; 514/331; 546/225; 546/235
[58] Field of Search .................... 546/232, 235, 546/225; 514/331, 330

[56] References Cited

U.S. PATENT DOCUMENTS

| | | | |
|---|---|---|---|
| 4,665,067 | 5/1987 | Kishimoto | 514/210 |
| 4,876,262 | 10/1989 | Oinuma | 514/318 |

FOREIGN PATENT DOCUMENTS

| | | |
|---|---|---|
| 0202164 | 11/1986 | European Pat. Off. |
| 0235752 | 2/1987 | European Pat. Off. |
| 0304888 | 3/1989 | European Pat. Off. |
| 320983 | 6/1989 | European Pat. Off. |
| 0437790 | 12/1990 | European Pat. Off. |

OTHER PUBLICATIONS

Burger, "A guide to the chemical basis of drug design", J. Wiley & Sons, (1984), p. 15.

*Primary Examiner*—Ceila Chang
*Attorney, Agent, or Firm*—Ruth E. Homan

[57] ABSTRACT

The present invention is direct to a new class of 1-piperidinyl alkanoarylsulfonamides of the formula I

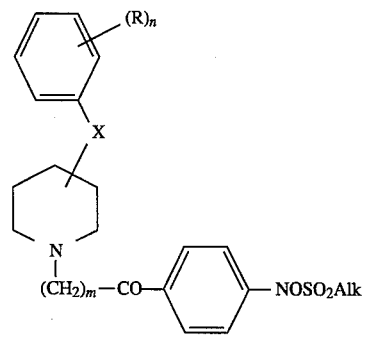

wherein R, X, m, n, and Alk are defined in the specification, and their use as antiarrhythmic agents.

30 Claims, No Drawings

1-PIPERIDINYL ALKANOYLANYL SULFONAMIDES FOR TREATMENT OF CARDIAC ARRHYTHMIA

This is a continuation of application Ser. No. 07/956,752, filed as PCT/US91/03323, May 15, 1991, now abandoned.

The present invention is directed to a new class of 1-piperidinyl alkanoylarylsulfonamide derivatives which are useful as Class III antiarrhythmic agents. Another aspect of the invention is directed to a method for treating cardiac arrhythmias. An additional aspect of the invention is directed to pharmaceutical compositions containing these compounds.

In accordance with the present invention a new class of antiarrhythmic agents have been discovered which can be described by the following formula:

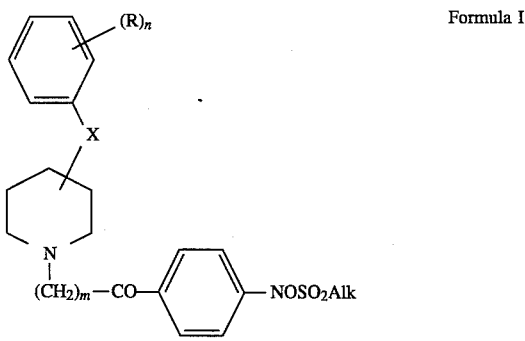

Formula I in which R is represented by hydrogen, halogen, $C_{1-4}$ alkyl, $C_{1-4}$ alkoxy, $CF_3$, $SR_1$, $NHC(O)R_2$, $NH_2$, or OH; $R_1$ is hydrogen or $C_{1-4}$ alkyl; $R_2$ is $C_{1-4}$ alkyl; X is represented by CO or CHOH; m is an integer from 1–3; n is an integer from 1–3; and Alk is a $C_{1-4}$ alkyl; and the pharmaceutically acceptable addition salts thereof.

As used in this application:

a) the term "halogen" refers to a fluorine, chlorine, or bromine atom;

b) the terms "lower alkyl group and $C_{1-4}$ alkyl" refer to a branched or straight chained alkyl group containing from 1–4 carbon atoms, such as methyl, ethyl, n-propyl, isopropyl, n-butyl, isobutyl, etc.;

c) the terms "lower alkoxy group and $C_{1-4}$ alkoxy" refer to a straight or branched alkoxy group containing from 1–4 carbon atoms, such as methoxy, ethoxy, n-propoxy, isopropoxy, n-butoxy, isobutoxy, etc.;

d) the term "pharmaceutically acceptable addition salt refers to either an acid addition salt or a basic addition salt;

e) the term "CO" refers to a carbonyl group having the following structure:

f) the term "CHOH" refers to a hydroxymethylene group;

g) the term "ketal" refers to the following substituent:

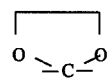

The expression "pharmaceutically acceptable acid addition salts" is intended to apply to any non-toxic organic or inorganic acid addition salt of the base compounds represented by Formula I or any of its intermediates. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tri-carboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, p-toluenesulfonic acid and sulfonic acids such as methanesulfonic acid and 2-hydroxyethane sulfonic acid. Either the mono- or di-acid salts may be formed, and such salts may exist in either a hydrated or substantially anhydrous form.

The expression "pharmaceutically acceptable basic addition salts" is intended to apply to any non-toxic organic or inorganic basic addition salts of the compounds represented by Formula I or any of its intermediates. Illustrative bases which form suitable salts include alkali metal or alkaline-earth metal hydroxides such as sodium, or potassium, and aliphatic or alicyclic amines, such as methylamine, dimethylamine, or trimethylamine. Either the mono- or di-basic salts may be formed with those compounds.

Some of the compounds of Formula I exist as optical isomers. Any reference in this application to one of the compounds represented by Formula I is meant to encompass either a specific optical isomer or a mixture of optical isomers. The specific optical isomers can be separated and recovered by techniques known in the art such as chromatography on chiral stationary phases, resolution via chiral salt formation and subsequent separation by selective crystallization or ester formation from a chiral acid followed by separation of the resultant diasterimoeric esters and hydrolysis to the desired enantiomer.

The X substituent may be bonded to either the 3-position or the 4-position of the piperidinyl ring. The phenyl ring adjacent to the 3- or 4-position of the piperidinyl ring may be optionally substituted. It is possible for this phenyl ring to contain up to 3 non-hydrogen substituents. These substituents can be located at any of the ortho, meta or para positions. These substituents can be the same or different.

Illustrative Examples of compounds encompassed by the present invention include:

N-[4-[[4-(2,3-dimethoxybenzoyl)-1-piperidinyl]acetyl]phenyl]methanesulfonamide,

N-[4-[[4-(3,4-difluorobenzoyl)-1-piperidinyl]acetyl]phenyl]methanesulfonamide,

N-[4-[[4-(2,4,6-trimethylbenzoyl)-1-piperidinyl]acetyl]phenyl]methanesulfonamide, N-[4-[[4-[4-(methylthio)benzoyl]-1-piperidinyl]acetyl]phenyl]methanesulfonamide, N-[4-[[4-(2-ethoxybenzoyl)-1-piperidinyl]acetyl]phenyl]methanesulfonamide, N-[4-[3-[4-[(3,4-difluorobenzoyl)-1-piperidinyl]-1-oxopropyl]phenyl]methansulfonamide, N-[4-[[4-[(2,3-dimethoxyphenyl)hydroxymethyl]-1-piperidinyl]acetyl]phenyl]methanesulfonamide, N-[4-[[4-[(4-fluorophenyl)hydroxymethyl]-1-piperidinyl]
acetyl]phenyl]methanesulfonamide, N-[4-[4-[4-(4-fluorobenzoyl)-1-piperidinyl]-1-oxobutyl]
phenyl]methanesulfonamide, N-[4-[[4-[(3,4-difluorophenyl)hydroxymethyl]-1-piperidi-
nyl]acetyl]phenyl]methansulfonamide, N-[4-[3-[4-[3,4-difluorophenyl)hydroxymethyl]-1-piperidi-
nyl]oxopropyl]phenyl]methanesulfonamide, N-[4-[3-[4-(4-fluorobenzoyl)-1-piperidinyl]-1-oxopropyl]-
phenyl]methanesulfonamide, N-[4-[[(4-fluorobenzoyl)-1-piperidinyl]-acetyl]phenyl]
methanesulfonamide, N-[4-[[(4-chlorobenzoyl)-1-piperidinyl]acetyl]-phenyl]
methanesulfonaminde, N-[4-[3-[(4-chlorobenzoyl)-1-piperidinyl]oxopropyl]phe-
nyl]methanesulfonamide, N-[4[3-[4-(4-fluorobenzoyl)-1-piperidinyl]1-oxopropyl]
phenyl]methanesulfonamide.

It is preferred for the compounds of Formula I to be 4-piperdino derivatives. It is preferred that R be represented by a 4-fluoro or a 3,4-difluorosubstituent. It is also preferred for m to be represented by 2.

The compounds of Formula I can be prepared using techniques which are analgously known in the art. One method for preparing these compounds is illustrated below in Reaction Scheme I:

REACTION SCHEME I

STEP A

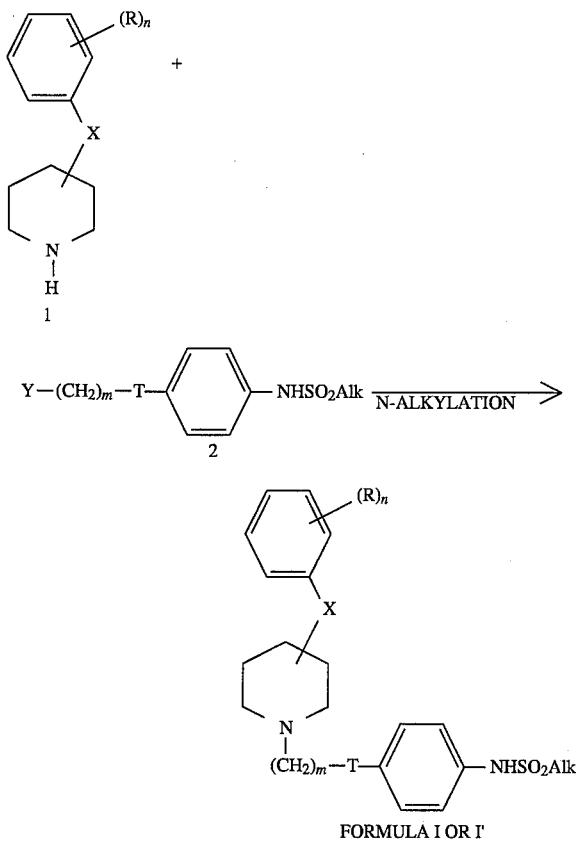

FORMULA I OR I'

-continued
REACTION SCHEME I

STEP B, OPTIONAL (Used if T = Ketal or
if R = —NHAc, —OAc, or —SAc)
(May be used if R is OCH₃
or SCH₃)

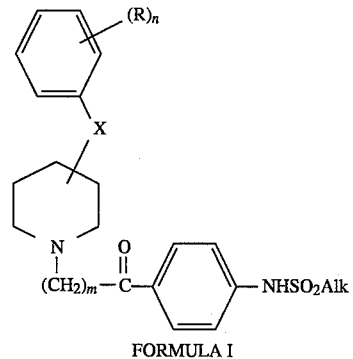

FORMULA I

I-T = CO
I'-T = ketal and/or
R = NHAc, OAc, —SAc₁, —OCH₃, or —SCH₃

In Step A of Reaction Scheme I, an N-alkylation reaction is carried out between a 3- or 4-substituted piperidine as described by structure 1, in which R and X are as in Formula I, and an N-alkylarylsulfonamide as described by structure 2, in which m and Alk are as in Formula I, Y is a leaving group such as a halogen atom or tosylate, and T is either CO or a ketal function, with the proviso that when R is to be OH, SH, or NH₂, then the corresponding acetyl derivative is utilized (i.e., OAc, NHAc, or SAc). If T is a ketal function or if R is an acetyl derivative, then it is necessary to carry out the optional Deprotection Reaction of Step B which converts any ketal function into a carbonyl group as is depicted and removes any acetyl function which leaves an OH, SH, or NH₂ substituent on the molecule.

The appropriate piperidinyl compound to utilize is one in which X and R are represented by the same substituent as is desired in the final product of Formula I or R is one of the acetyl functions identified above. X should be bonded to the 3- or 4- position as is desired in the final product. The appropriate N-alkylarylsulfonamide is one in which Alk and m are represented by the same substituent as is desired in the final product. The particular leaving group that Y represents is not critical since it is not retained in the final product. If m is represented 1 or 2, then T should be represented by CO. If m is to be represented by 3, then T should be represented by a ketal which serves to prevent cyclopropane formation.

For example if the desired product is, N-[4-[3-[4-(4-fluorobenzoyl-1 -piperidinyl]-1-oxopropyl]phenyl]-methanesulfonamide, then the proper reactants are 4-fluorophenyl-4-piperidinyl methanone and N-[4-(3-chloro-1-oxopropyl)phenyl]methanesulfonamide. N-[4-[4-[4-(4-fluorobenzoyl-1-piperidinyl] -1-oxobutyl]phenyl]-methanesulfonamide can be produced by reacting 4-fluorophenyl-4-piperidinyl methanone and 2-(3-chloro-propyl)-2-(4-methanesulfonamidophenyl) 1,3-dioxolane.

The N-alkylation can be carried out using techniques known in the art. Approximately equivalent amounts of the piperidinyl compound of structure 1 and the alkanoylarylsulfonamide of structure 2 are contacted in a solvent such as aqueous tetrahydrofuran, n-butanol, toluene or dimethylformamide, etc. The reaction is carried out in the presence of at least one equivalent of a weak base such as potassium bicarbonate, potassium carbonate or sodium bicarbonate. If desired the N-alkylation can be carried out in the presence of a catalytic amount of potassium iodide. The reaction is typically carried out at a temperature range of from room temperature to reflux for a period of time ranging from 1 hour to 5 days.

The crude product of Formula I or I' can be recovered from the reaction medium and purified by techniques known in the art. For example, the crude compounds can be recovered by organic solvent extraction in the presence of Water. Suitable extraction solvents include ethyl acetate, dichloromethane or chloroform. The resulting crude material can then be purified by recrystallization from a solvent system such as methanol, methanol/butanone, isopropanol or chloroform, etc. The compounds may also be purified by chromatographic techniques such as silica gel chromatography. Suitable chromatographic solvents include ethyl acetate, acetone, ethyl acetate/hexane, or ethyl acetate/acetone.

The Optional Deprotection Reaction of Step B can also be carried out using techniques known in the art. Typically the crude product of Formula I' in which X is CO is subjected to an acidic hydrolysis with a mineral acid such as HCL (about 0.1–0.5 N in methanol). The hydrolysis is typically carried out at a temperature range of from 0° to 30° C. for a period of time ranging from 0.5 to 5 hours. If X is represented by CHOH, then a mild organic acid such as tartaric acid should be utilized. Typically a slight molar excess of the organic acid is utilized in a solvent such as aqueous THF at a temperature of about 0° C. for about 0.5 hours. After either hydrolysis is completed, the reaction medium is neutralized with a mild base such as sodium bicarbonate. The resulting compound of Formula I can be recovered and purified by the same methods taught in Step A of Reaction Scheme I.

Methods for producing the N-alkylarylsulfonamides of structure 2 are known in the art. Methods for producing the 3- and 4-substituted piperidines of structure 1 are known in the art. For example, those in which X is CO may be prepared by carrying out a Friedel-Craft reaction between an appropriately substituted benzene and isonipecetic acid chloride HCl Reaction of an appropriately substituted phenyl Grignard reagent with 3- or 4-cyano-1-trifluoroacetylpiperidine is also suitable, followed by deprotection with Na₂CO₃/methanol. Those compounds in which X is CHOH may then be produced by reducing ketones produced above. Appropriate reduction techniques include either catalytic hydrogenation or hydride reducing agents such as sodium borohydride.

These reactions are well known in the art and are illustrated in U.S. Pat. No. 4,783,471 which is hereby incorporated by reference.

Alternatively, as illustrated below in Reaction Scheme II, the 3- and 4-substituted piperidines of structure 1 in which X is CHOH can be prepared by reacting an appropriately substituted phenyl magnesium bromide (structure 3; Grignard Reagent) with 3- or 4-pyridine carboxaldehyde, structure (4), as is known in the art, thereby producing the carbinol of structure (5). This compound is catalytically reduced as is known in the art which produces the substituted piperidines of structure 1 in which X is CHOH. Oxidation with CrO₃ will produce the corresponding ketone.

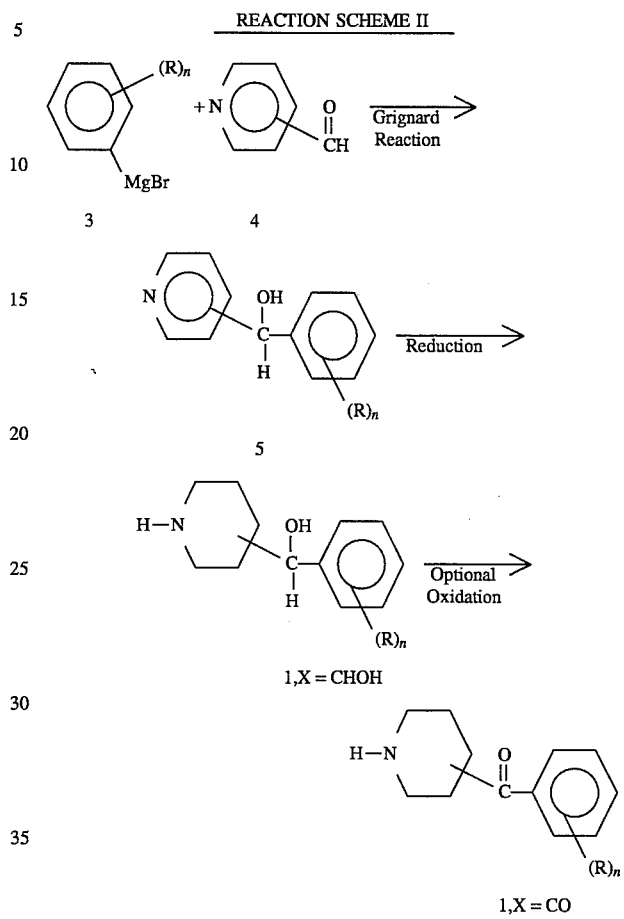

REACTION SCHEME II

Another method for producing the 3- and 4-substituted piperidines of structure 1 in which X is CO is the following 3-step synthesis illustrated below in Reaction Scheme III. In Step A, an acylation reaction is carried out between 1-(1,1-dimethylethyl)-1,3-(or 4)-piperidinedicarboxylic acid, structure (6), and N,O-dimethylhydroxylamine hydrochloride, structure (7), in the presence of 1,1-carboxyldimidazole. The reactants are present in an equivalent amount and the reaction is carried out at room temperature under a nitrogen atmosphere in methylene dichloride. The piperidine of structure (6) is first contacted with the 1,1-carbonyldimidazole for about 1 hour. The hydroxylamine of structure (7) is then added and the reactants are stirred together for 1–12 hours. The resulting 3- or 4-N-methoxy-N-methyl-carboxamido)-1-piperidinecarboxylic acid 1,1-dimethylethylester, structure (8) can be recovered by acidification, extraction and then purified by distillation.

In Step B, a appropriately substituted benzene derivative (or bromo-substituted benzene derivative) is contacted with n-butyl lithium at about 0° C. under an argon atmosphere for about 1 hour. The reaction is then cooled to −78° C. and an equivalent amount of the product of Step A is added to the reaction. Upon completion of the addition, the reaction is warmed to room temperature and stirred for approximately 3 hours. This displacement reaction produces an N-protected piperidine of structure (1) in which X is CO. It can be recovered by extraction and purified by silica gel chromatography. In Step C, the protecting group at the 1-position of the piperidine ring is removed by hydrolysis with trifluoroacetic acid as is known in the art.

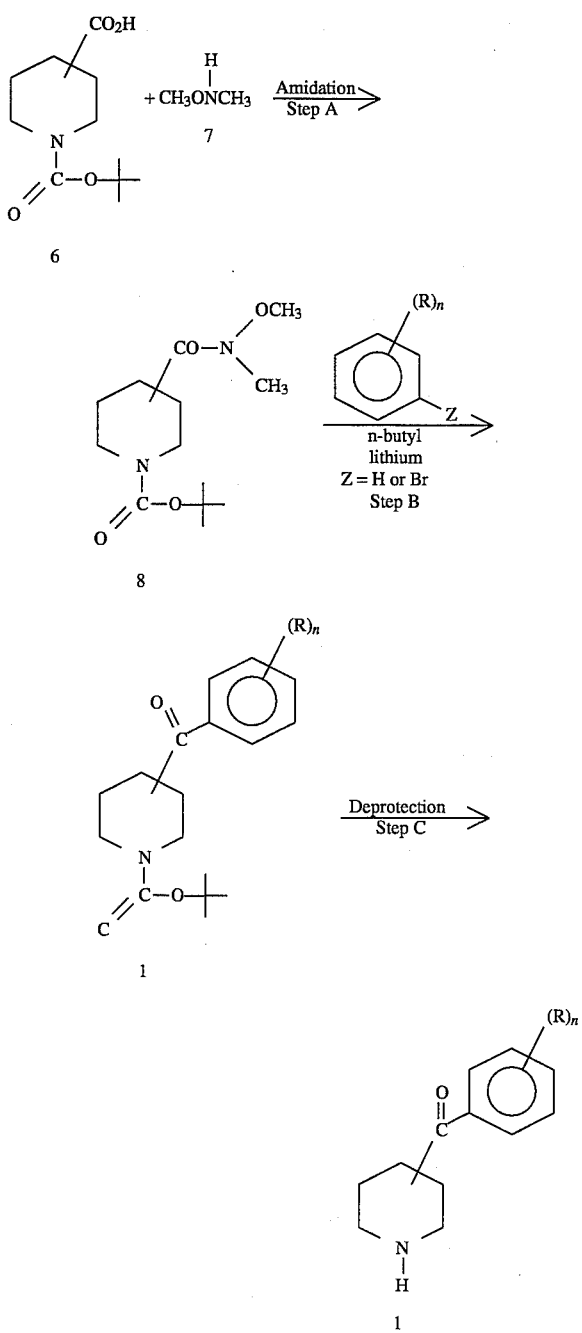

The compounds of Formula I are useful as cardiac antiarrhythmic agents. They can be administered to a patient suffering from an arrhythmic episode in order to terminate that episode and return the myocardium to a normal sinus rhythm. The compounds can also be administered on a prophylactic basis to prevent the occcurence of arrhythmic episodes.

The compounds of Formula I increase the duration of the action potential of myocardial tissue producing an increase in the refractory period of that tissue. Thus, under the classification system of Vaughan Williams these compounds exhibit a Class III antiarrhythmic activity.

One method of demonstrating the antiarrhythmic activity of these compounds is the following test protocol. This protocol demonstrates what effect a compound has upon the action potential of isolated cardiac tissue, such as a Purkinje fiber from a dog heart or a papillary muscle from a guinea pig heart.

The heart of an anesthetized mongrel dog is surgically removed and the Purkinje fibers are dissected from either of the ventricles. Alternatively, papillary muscles are removed from the right cardiac ventricle of a guinea pig. A Purkinje fiber or a papillary muscle is then placed in a tissue bath which is continuously perfused with modified Tyrode's solution. The modified Tyrode's solution has the following composition (in mM): NaCl 127.0, KCl 15.4, $NaH_2PO_4$ 0.5, $MgCl_2$ 1.0, $NaHCO_3$ 23.8, $CaCl_2$ 1.8 and glucose 11.1. A gas mixture comprised of 95% $O_2$ and 5% $CO_2$ is bubbled through the solution while it is maintained within a pH range of from 7.3–7.4.

The electrophysiology of the cardiac tissue is monitored by conventional glass microelectrodes. One microelectrode is inserted into a cell in the cardiac muscle fiber and a ground electrode is positioned in the tissue bath. A conventional oscilloscope is utilized to visualize the action potential waveforms of the cardiac cell.

The cardiac muscle fiber is electrically stimulated at a frequency of 1 Hz through a pair of platinum plates placed in the tissue bath. This stimulation is continued for approximately 1 hour in order to allow the electrophysiological characteristics of the fiber to stabilize.

After-approximately 1 hour, the fiber should be exhibiting a stable action potential as demonstrated by the waveform displayed on the oscilloscope. At this point, representative control action potentials are recorded and analyzed by a computer.

After establishing a control action potential, the test compound is introduced into the Modified Tyrode's solution in a quantity such that the test compound is present within the tissue bath in a range of from $10^{-8}$ to $10^{-5}$ moles/liter. After the effect of the test compound has reached a steady state, the action potential is again recorded and analyzed in the manner described above.

The in vivo antiarrhythmic activity of the compounds can be demonstrated in the following manner. Mongrel dogs of either sex are anesthetized with sodium pentobarbitol (35 mg/kg, i.v.). The dogs are respirated and the heart is exposed via a thoracotomy. Two pairs of plunge electrodes are placed in the mid-myocardium of the left ventricle for introduction of ventricular extra-stimuli. Two additional pairs of plunge electrodes are placed in the mid-myocardium within 1–2 mm of the ventricular pacing electrodes for recording local bipolar ventricular electrograms. Bipolar electrograms are recorded with the low and high frequency cutoffs set at 30 and 90 Hz, respectively. A pair of stainless steel electrodes are sutured onto the right atrial appendage for pacing the heart. The sinoatrial node is crushed, and the heart is paced at 150 beats per minute (5 msec duration, twice diastolic threshhold voltage or current). The local bipolar electrogram, as well as the Lead II ECG, is recorded continuously on a polygraph, and also acquired by a computer.

Ventricular effective refractory period (ERP) is determined by introduction of a single ventricular extrastimulus (4 msec duration, twice diastolic threshhold voltage or current) at progressively shorter delays after the right atrial stimulus, until a propagated ventricular depolarization is not seen in the Lead II ECG.

The ERP is defined as the longest interval between the ventricular extrastimulus that does not result in a propagated ventricular depolarization, and the preceding ventricular depolarization. The ERP is measured by the computer using the local bipolar electrogram from the site adjacent to ventricular stimulating electrodes. ERP's are determined at two sites in each heart and the values averaged. ERP's are initially determined under pretreatment conditions. Test compound is then administered either intravenously via a cannula placed in the right femoral vein, or intraduodenally via a cannula placed in the duodenum. ERP's are redetermined following the administration of that compound. The compounds of Formula I will increase the ERP.

The compounds of the present invention having Class III antiarrhythmic properties are useful for treating a variety of arrhythmic conditions of the heart. Representative examples of arrhythmic conditions which are amendable to treatment with the compounds of the present invention include supraventricular arrhythmias such as atrial tachycardia, atrial flutter, atrial fibrillation and paroxosysmal supraventricular tachycardia, and ventricular arrhythmias such as premature ventricular complexes, and life threatening ventricular arrhythmias such as ventricular tachycardia, or ventricular fibrillation. These compounds will also prevent recurrent episodes of the arrhythmias mentioned above.

The quantity of compound needed to either terminate an arrhythmic episode or prevent the occurrence of an arrhythmic episode (i.e., an antiarrhythmic quantity) will vary depending upon the route of administration, the patient, the severity of the patient's condition, the presence of other underlying disease states, and the particular compound utilized. However as a general guideline, if the compound is being administered orally, then it is preferably administered within a dosage range of from about 0.1 to about 100 mg/kg of patient body weight/day. Likewise, if the compound is being administered parenterally then it is preferably administered within a dosage range of from about 0.01 to about 10.0 mg/kg of patient body weight/day.

Repetitive daily administration may be desirable. Typically, the compounds will be administered from 1–4 times daily. They can also be administered as a continuous drip in critical care environments. The patient's response to the compound can be monitored via an EKG or any other technique conventionally used in the art.

As used in this application:

a) the term "arrhythmia" refers to any variation from the normal rhythm of the heart beat, and;

b) the term "antiarrhythmic" refers to a compound capable of either preventing or alleviating an arrhythmia.

For oral administration, the compounds can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations. In another embodiment, the compounds of Formula I can be tabletted with conventional tablet bases such as lactose, sucrose, and cornstarch in combination with binders, such as acacia, cornstarch, or gelatin, disintegrating agents such as potato starch or algenic acid, and a lubricant such as stearic acid or magnesium stearate. Liquid preparations are prepared by dissolving the active ingredient in an aqueous or non-aqueous pharmaceutically acceptable solvent which may also contain suspending agents, sweetening agents, flavoring agents, and preservative agents as are known in the art.

For parenteral administration, the compounds may be dissolved in a physiologically acceptable pharmaceutical carrier and administered as either a solution or a suspension. Illustrative of suitable pharmaceutical carriers are water, n-saline, dextrose solutions, fructose solutions, ethanol, or oils of animal, vegetative, or synthetic origin. The pharmaceutical carrier may also contain preservatives, buffers, etc. as are known in the art.

The compounds of Formula I may be admixed with any inert carrier and utilized in laboratory assays in order to determine the concentration of the compounds within the urine, serum, etc. of the patient as is known in the art.

The following examples are presented in order to further illustrate the present invention. However, they should not be construed as limiting the scope of the invention in any manner.

EXAMPLE I

This example demonstrates one of the N-alkylation reactions of Reaction Scheme I.

A) N-[4[3-[4-(4-Fluorobenzoyl)-1-piperidinyl]1-oxopropyl]phenyl]methanesulfonamide monohydrochloride A mixture of 4-fluorophenyl-4-piperidinyl methanone (3.30 g, 15.9 mmol) and N-[4-(3-chloro-1-oxopropyl)phenyl]methanesulfonamide was prepared in n-butanol (100 mL), treated with potassium bicarbonate (1.60 g, 1.6.0 mmol) and a catalytic amount of potassium iodide and refluxed for 18 hours. The mixture was cooled to room temperature and evaporated at reduced pressure onto neutral alumina. The resulting solid was put on top of a column of silica gel and eluted with acetone. The appropriate fractions were combined and evaporated to afford an orange oil. The oil was dissolved in ethyl acetate, dried (MgSO$_4$), filtered, and treated with a slight excess of HCl in EtOAc. The resulting solid was filtered and recrystallized from methanol to yield the desired product as tan crystals: mp 230°–236° C. (decomp.).

EXAMPLE 2

This example demonstrates one of the N-alkylation reactions of Step A and one of the deprotection reactions of Step B.

N-[4-[4-[4-(4-Fluorobenzoyl)-1-piperidinyl]-1-oxobutyl]phenyl]methanesulfonamide monohydrochloride A mixture of 4-fluorophenyl-4-piperidinyl methanone (3.1 g, 15.0 mmol) and 2-(3-chloropropyl)-2-(4-methanesulfonamidophenyl)-1,3-dioxolane (4.70 g, 14.7 mmol) was prepared in n-butanol (50 mL), treated with potassium carbonate (2.00 g, 14.5 mmol) and a catalytic amount of potassium iodide, and refluxed for 18 hours. The cooled mixture was diluted with water and ethyl acetate. The layers were separated and the aqueous layer was extracted with ethyl acetate. The combined organic layers were washed with water, brine, dried (MgSO$_4$), filtered, and evaporated to an oil. The oil was dissolved in methanol (200 mL), treated with HCl (25 mL of a 10% solution in water), and stirred for 5 hours. The solution was concentrated, made basic with aqueous 5% sodium bicarbonate, and extracted twice with chloroform. The combined organic layers were washed with water, brine, dried (MgSO₄), filtered, and evaporated to a yellow solid. The solid was chromatographed on silica gel, eluting with acetone. The appropriate fractions were combined and evaporated to afford a yellow solid. The solid was dissolved in methanol and treated with a slight excess of HCl in methanol. The solution was concentrated and the resulting solid was recrystallized from methanol/butanone to yield the desired product as a tan powder: mp 205°–210° C. (decomp.).

EXAMPLE 3

This example demonstrates the preparation of

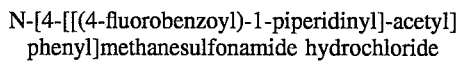

N-[4-[[(4-fluorobenzoyl)-1-piperidinyl]-acetyl] phenyl]methanesulfonamide hydrochloride To a solution of 3.4 g (14.1 mmol) of 4-fluorobenzoylpiperidine hydrochloride in 150 mL THF and 30 mL of water was added 5 g (59 mmol) of sodium bicarbonate followed by 3.5 g (14.1 mmol) of 2-chloro-4'-methanesulfonamidoacetophenone. After refluxing for 3.5 hours, the reaction was concentrated to ½ volume on a rotary evaporator. The mixture was extracted with chloroform, the organic layer dried with magnesium sulfate and concentrated. The resulting thick oil was treated with methanolic hydrogen chloride. The hydrochloride salt so obtained was recrystallized from methanol/2-butanone to give N-[4-[[(4-fluorobenzoyl)-1-piperidinyl]-acetyl] phenyl]methanesulfonamide hydrochloride as a white solid: mp 276°–280° C. (d).

EXAMPLE 4

N-[4-[[4-(2,3-Dimethoxybenzoyl)-1-piperidinyl] acetyl]phenyl]-methanesulfonamide monohydrochloride A solution of 4-(2,3-dimethoxy-phenyl)-4-piperidinylmethanone trifluoroacetate (2.0 g, 5.5 mmol), N-[4-(2-chloro-1-oxoethyl)phenyl]methanesulfonamide (1.19 g, 5.5 mmol) and KHCO₃ (1.1 g, 11 mmol) was prepared in THF (75 mL) and H₂O (25 mL) and refluxed for 2 hours. The solution was concentrated and the resulting slurry was diluted with water and CH₂Cl₂. The partition was filtered through a glass filter and the resulting white solid was washed with CH₂Cl₂ and water. The white solid was dried overnight.

The layers of the filtrate were separated and the organic layer was washed with brine, dried (MgSO₄) and evaporated to a yellow foam. The yellow foam and white powder were combined and chromatographed on silica gel eluting with 10% hexane in ethyl acetate. Evaporation of the appropriate fractions produced a white powder. The powder was dissolved in THF and treated with ethereal HCl to afford a white powder. The salt was recrystallized from methanol to afford N-[4-[[4-(2,3-dimethoxybenzoyl)-1-piperidinyl] acetyl]phenylmethanesulfonamide monohydrochloride as fine white needles, m.p. 242°–252° C. (decomp.). Anal. Calcd for $C_{23}H_{28}N_2O_6S \cdot HCl$: C, 55.58; H, 5.88; N, 5.64. Found: C, 55.45; H, 5.96; N, 5.75

EXAMPLE 5

N-[4-[[4-[(2,3-Dimethoxyphenyl)hydroxymethyl]-1-piperidinyl]acetyl]phenyl]methanesulfonamide monohydrochloride To a stirred solution of α-(2,3-dimethoxyphenyl)-4-piperidine methanol (2.0 g, 8.0 mmol) in THF (60 mL) was added KHCO₃ (0.80 g, 8.0 mmol), then H₂O (6 mL), then N-[4-( 2-chloro-1-oxoethyl)phenyl]methanesulfonamide (1.73 g, 8.0 mmol). After stirring overnight, the solution was concentrated, diluted with water, then extracted twice with CH₂Cl₂. The combined organic layers were dried (MgSO₄), and concentrated to 30 mL. This organic solution was chromatographed on silica gel, eluting with ethyl acetate.

The appropriate fractions were evaporated to a white foam. The foam was crystallized from isopropanol at reduced temperature and the resulting crystals were filtered under a nitrogen atmosphere and then washed with hexane. The resulting yellow solid was dried, producing N-[4-[[4-[(2,3-Dimethoxyphenyl)hydroxymethyl]-1-piperidinyl] acetyl]phenyl]methanesulfonamide monohydrochloride, m.p. 94°–95° C. Anal. Calcd for $C_{23}H_{30}N_2O_6S$ (462.56): C, 59.72; H, 6.54; N, 6.06. Found: C, 59.58; H, 6.68, N, 5.94.

Using the methodology above, but substituting the appropriate starting materials, N-[4-[[4-[(4-fluro phenyl)hydroxymethyl] -1-piperidinyl]acetyl]phenyl]methane sufonamide, mp 85°–100° C., was obtained.

EXAMPLE 6

N-[4-[[4-(3,4-Diflourobenzoyl)-1-piperidinyl]acetyl] phenylmethanesulfonamide monohydrochloride A solution of 4-(3,4-difluorophenyl)-4-piperidinylmethanone hydrochloride (5.00 g, 19.1 mmol) and N-[4-(2-chloro-1-oxoethyl)phenyl]methanesulfonamide (5.2 g, 21.0 mmol) was prepared in THF (120 mL) and H₂O (20 mL), treated with KHCO₃ (4.00 g, 40 mmol) and stirred overnight for 5 days. The solution was concentrated, diluted with water, then extracted twice with CH₂Cl₂. The combined organic layers were dried (MgSO₄), and evaporated to an off-white powder which was dissolved in 300 mL of hot methanol. The solution was filtered and concentrated onto 40 g of neutral alumina. The alumina was put on top of a column of silica gel and eluted with 20% hexane in EtOAc.

The appropriate fractions were combined and treated with ethereal HCl. The resulting solid was recrystallized from methanol to afford 4.4 g of N-[4-[[4-(3,4-difluorobenzoyl)-1-piperidinyl]acetyl]phenyl]methanesulfonamide monohydrochloride as a pale yellow powder. m.p. >250° C. (decomp.). Anal. calcd for $C_{21}H_{22}F_2N_2O_4S \cdot HCl$: C, 53.33; H, 4.90; N, 5.92. Found: C, 53.28; H, 4.93; N, 5.82.

EXAMPLE 7

N-[4-[[4-(2,4,6-Trimethylbenzoyl)-1-piperidinyl] acetyl]phenyl]methanesulfonamide monohydrochloride A solution of 4-(2,4,6-trimethylphenyl)-4-piperidinylmethanone monohydrochloride (2.5 g, 9.3 mmol) and N-[4-(2 -chloro-1-oxoethyl)phenyl]methanesulfonamide (2.54 g, 10.3 mmol) was prepared in THF/H₂O (60/10), treated with KHCO₃ (2.0 g, 20 mmol), and stirred for 2 days. The solution was concentrated, diluted with water, then extracted twice with CHCl₃. The combined organic layers were dried (MgSO₄), and evaporated to a tan foam. The foam was chromatographed on silica gel and eluted with 25% hexane in EtoAc.

The appropriate fractions were combined and evaporated to afford a yellow solid. The solid was dissolved in methanol and treated with HCl/methanol. The solution was concentrated and the resulting solid was recrystallized from methanol to afford N-[4-[[4-(2,4,6-trimethylbenzoyl)-1-piperidinyl]-acetyl]phenyl]methanesulfonamide monohydrochloride as white needles, m.p. >260° C. (decomp.). Anal. calcd for $C_{24}H_{30}N_2O_4S \cdot HCl$: C, 60.18; H, 6.52; N, 5.85. Found: C, 60.37; H, 6.67; N, 5.71.

EXAMPLE 8

N-[4-[[4-(4-Methylthio)benzoyl]-1-piperidinyl]acetyl]phenyl]-methanesulfonamide monohydrochloride A solution of 4-methylthiophenyl-4-piperidinylmethanone monohydrochloride (5.00 g, 18.4 mmol), N-[4-(2-chloro-1-oxoethyl)phenyl]methanesulfonamide (5.00 g, 20.2 mmol), and $KHCO_3$ (3.8 g, 38 mmol) was prepared in aqueous THF (120 mL THF/20 mL $H_2O$) and stirred for 2 days. The solution was concentrated, diluted with water, then extracted twice with $CHCl_3$. The combined organic layers were dried ($MgSO_4$), and evaporated to afford a foam. The foam was chromatographed on silica gel and eluted with 3:1 EtoAc:hexane.

The appropriate fractions were combined and evaporated to afford a solid. The solid was dissolved in methanol and treated with HCl/methanol. The solution was concentrated and the resulting solid was recrystallized from methanol to afford N-[4-[[4-(4-(methylthio)benzoyl]-1-piperidinyl]acetyl]phenyl]-methanesulfonamide monohydrochloride as light rose colored flakes, m.p. >260° C. (decomp.). Anal. Calcd for $C_{22}H_{26}N_2O_4S_2 \cdot HCl$. C, 54.70; H, 5.63; N, 5.80. Found: C, 54.81; H, 5.68; N, 5.72.

Utilizing the methodology of Example 8 but substituting the appropriate starting materials the following compounds may be prepared:

a) N-[4[[4-(4-chlorobenzoyl)-1-piperidinyl]acetyl]phenyl]methanesulfonamide hydrochloride m.p. >250° C. (dec.);

b) N-[4[[4-(4-acetamidobenzoyl)-1-piperidinyl]acetyl]phenyl]methanesulfonamide m.p. 200–210 (dec.);

c) N-[4[[4(4-aminobenzoyl)-1-piperidinyl]acetyl]phenyl]methanesulfonamide hydrochloride m.p. 230°–250° C.;

d) N-[4[[4-(3,4-difluorobenzoyl)-1-piperodinyl]oxopropyl]phenyl]methanesulfonamide m.p. >137°–138° C. (dec.);

e) N-[4[[4-(2-ethoxybenzoyl)-1-piperidinyl]acetyl]phenyl]methanesulfonamide m.p. 155°–156° C. (dec.);

f) N-[4[[3-(2-methoxybenzoyl)-1-piperidinyl]acetyl]phenyl]methanesulfonamide hydrochloride m.p. 245°–247° C. (dec.);

g) N-[4[[3-(4-fluorobenzoyl)-1-piperidinyl]acetyl]phenyl]methanesulfonamide;

h) N-[4[[3-(3,4-difluorobenzoyl)-1-piperidinyl]acetyl]phenyl]methanesulfonamide;

i) N-[4[[3-(4-chlorobenzoyl)-1-piperidinyl]acetyl]phenyl]methanesulfonamide;

j) N[4[[3-(4-methylthiobenzoyl)-1-piperidinyl]acetyl]phenyl]methanesulfonamide.

What is claimed is:
1. A compound of the formula:

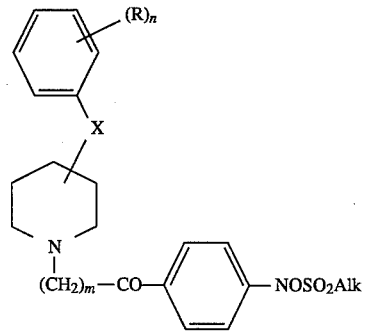

in which R is represented by hydrogen, halogen, $C_{1-4}$ alkyl, $C_{1-4}$ alkoxy, $CF_3$, $SR_1$, or OH; $R_1$ is hydrogen or $C_{1-4}$ alkyl; X is represented by CO or CHOH; m is an integer from 1–3; n is an integer from 1–3; and Alk is a $C_{1-4}$ alkyl; and the pharmaceutically acceptable addition salts thereof.

2. A compound according to claims 1 wherein X is CHOH.

3. A compound according to claims 1 wherein X is CO.

4. A compound according to claim 3 wherein m is 1.

5. A compound according to claim 3 wherein m is 2.

6. A compound according to claim 5 wherein Alk is methyl.

7. A compound according to claim 1 wherein said compound is N-[4-[[4-(2,3-dimethoxybenzoyl)-1-piperidinyl]acetyl]-phenyl]methanesulfonamide.

8. A compound according to claim 1 wherein said compound is N-[4-[[4-(3,4-difluorobenzoyl)-1-piperidinyl]acetyl]-phenyl]-methanesulfonamide.

9. A compound according to claim 1 wherein said compound is N-[4-[[4-(2,4,6-trimethylbenzoyl)-1-piperidinyl]acetyl]-phenyl]methanesulfonamide.

10. A compound according to claim 1 wherein said compound is N-[4-[[4-[4-(methylthio)benzoyl]-1-piperidinyl]acetyl]-phenyl]methanesulfonamide.

11. A compound according to claim 1 wherein said compound is N-[4-[[4-(2-ethoxybenzoyl)-1-piperidinyl]acetyl]phenyl]-methanesulfonamide.

12. A compound according to claim 1 wherein said compound is N-[4-[[4-[(2,3-dimethoxyphenyl)hydroxymethyl]-1-piperidinyl]acetyl]phenyl]methanesulfonamide.

13. A compound according to claim 1 wherein said compound is N-[4-[[4-[(4-fluorophenyl)hydroxymethyl]-1-piperidinyl]-acetyl]phenyl]methanesulfonamide.

14. A compound according to claim 1 wherein said compound is N-[4-[4-[4-(4-fluorobenzoyl)-1-piperidinyl]-1-oxobutyl]-phenyl]methanesulfonamide monohydrochloride.

15. A compound according to claim 1 wherein said compound is N-[4-[3-[4-(4-fluorobenzoyl)-1-piperidinyl]-1-oxopropyl]phenyl]methanesulfonamide monohydrochloride.

16. A compound according to claim 1 wherein said compound is N-[4-[3-[4-(4-fluorobenzoyl)-1-piperidinyl]-1-oxopropyl]phenyl]methanesulfonamide.

17. A compound according to claim 1 wherein said compound is N-[4-[[(4-chlorobenzoyl)-1-piperidinyl]acetyl]phenyl]-methanesulfonamide.

18. A compound according to claim 1 wherein said compound is N-[4-[3-[(4-chlorobenzoyl)-1-piperidinyl]oxopropyl]-phenyl]methanesulfonamide.

19. A compound according to claim 1 wherein said compound is N-[4-[3-[4-[(3,4-difluorobenzoyl)-1-piperidinyl]-1-oxopropyl]-phenyl]methansulfonamide.

20. A compound according to claim 1 wherein said compound is N-[4-[[4-[(3,4-difluorophenyl)hydroxymethyl]-1-piperidinyl]acetyl]phenyl]methansulfonamide.

21. A compound according to claim 1 wherein said compound is N-[4-[3-[4-[3,4-difluorophenyl)hydroxymethyl]-1-piperidinyl]oxopropyl]phenyl]methanesulfonamide.

22. A compound according to claim 1 wherein said compound is N-[4[3-[4-(4-fluorobenzoyl)-1-piperidinyl]1-oxopropyl] phenyl]methanesulfonamide.

23. A compound according to claim 1 wherein said compound is N-[4[[3-(2-methoxybenzoyl)-1-piperidinyl] acetyl]phenyl]methanesulfonamide hydrochloride.

24. A compound according to claim 1 wherein said compound is N-[4[[3-(4-fluorobenzoyl)-1-piperidinyl] acetyl]phenyl]methanesulfonamide.

25. A compound according to claim 1 wherein said compound is N-[4[[3-(3,4-difluorobenzoyl)-1-piperidinyl] acetyl]phenyl]methanesulfonamide.

26. A compound according to claim 1 wherein said compound is N-[4[[3-(4-chlorobenzoyl)-1-piperidinyl] acetyl]phenyl]methanesulfonamide.

27. A compound according to claim 1 wherein said compound is N-[4-[[4-[(4-flurophenyl)hydroxymethyl]-1-piperidinyl]acetyl]phenyl]methane sufonamide.

28. A compound according to claim 1 in which X is bonded to the 4-position of the piperidine ring.

29. A method for the treatment of cardiac arrhythmias comprising administering to a patient in need therof an effective amount of a compound according to claim 1.

30. A pharmaceutical composition comprising an effective amount of a compound according to claim 1 in admixture with a pharmaceutically acceptable carrier.

* * * * *

UNITED STATES PATENT AND TRADEMARK OFFICE
CERTIFICATE OF CORRECTION

PATENT NO. : 5,478,846
DATED : December 26, 1995
INVENTOR(S) : Carr, et al

It is certified that error appears in the above-indentified patent and that said Letters Patent is hereby corrected as shown below:

Column 1, Line 6 and 7 reads: "This is a continuation of application Ser. No. 07/956,752, filed as PCT/US91/03323, May 15, 1991, now abandoned."

should read

-- This application is a continuation of application Ser. No. 07/956,752 filed September 13, 1993, now abandoned, which had an effective international filing date of May 15, 1991 as application PCT/US91/03323, which is a CIP of application serial number 07/534,784 filed on June 7, 1990, now abandoned.--

Signed and Sealed this

Fifteenth Day of October, 1996

Attest:

BRUCE LEHMAN

*Attesting Officer*    *Commissioner of Patents and Trademarks*